(12) United States Patent
Scheck et al.

(10) Patent No.: US 10,398,171 B2
(45) Date of Patent: Sep. 3, 2019

(54) DEVICE FOR ADJUSTING AN AMOUNT OF AN ACTIVE SUBSTANCE INHALED BY A USER AND COMMUNICATING PORTABLE TERMINAL

(71) Applicant: ENOVAP, Rosières-Près-Troyes (FR)

(72) Inventors: Alexandre Scheck, Paris (FR); Philippe Lemail, Paris (FR); Vincent Devos, Paris (FR); Joseph Elkhoury, Paris (FR); Murat Suna, Paris (FR); Céline Kayal, Paris (FR)

(73) Assignee: ENOVAP, Rosieres-Pres-Troyes (FR)

( * ) Notice: Subject to any disclaimer, the term of this patent is extended or adjusted under 35 U.S.C. 154(b) by 174 days.

(21) Appl. No.: 15/301,736

(22) PCT Filed: Mar. 31, 2015

(86) PCT No.: PCT/FR2015/050839
§ 371 (c)(1),
(2) Date: Oct. 4, 2016

(87) PCT Pub. No.: WO2015/150699
PCT Pub. Date: Oct. 8, 2015

(65) Prior Publication Data
US 2017/0027232 A1 Feb. 2, 2017

(30) Foreign Application Priority Data

Apr. 4, 2014 (FR) ..................................... 14 00817

(51) Int. Cl.
*A24F 47/00* (2006.01)
*A61M 15/00* (2006.01)
(Continued)

(52) U.S. Cl.
CPC ....... *A24F 47/008* (2013.01); *A61M 15/0065* (2013.01); *A61M 15/06* (2013.01);
(Continued)

(58) Field of Classification Search
CPC ................ A24F 47/008; H05B 1/0244; H05B 2203/021; A61M 15/06; A61M 15/0065; A61M 2230/20; A61M 2205/36
See application file for complete search history.

(56) References Cited

U.S. PATENT DOCUMENTS 5,894,841 A * 4/1999 Voges .................. A24F 47/008
128/203.12
6,202,642 B1 * 3/2001 McKinnon .......... A61M 15/009
128/200.14
(Continued)

FOREIGN PATENT DOCUMENTS

EP 2 609 820 A1 7/2013

*Primary Examiner* — Seyed Masoud Malekzadeh
*Assistant Examiner* — Taryn Trace Willett
(74) *Attorney, Agent, or Firm* — Patshegen IP LLC; Moshe Pinchas (57) ABSTRACT

A device to adjust an amount of an active substance inhaled by a user includes two tanks. A first tank includes a liquid having a lower density of active substance than a liquid in the second tank. Each liquid is configured to evaporate when the liquid is heated beyond a predefined temperature limit. An inhaler to inhale the liquid vapor evaporating from each tank by the user. One heating resistor is associated with each tank. A controller to control the heating of each resistor to actuate each resistor independently in accordance with the determined amount of active substance to be vaporized. The ratio of the heating of the resistor of the second tank to the heating of the resistor of the first tank is an increasing function of the determined amount of active substance to be vaporized.

9 Claims, 5 Drawing Sheets

(51) Int. Cl.
  *A61M 15/06* (2006.01)
  *H05B 1/02* (2006.01)
(52) U.S. Cl.
  CPC ....... H05B 1/0244 (2013.01); *A61M 2205/36* (2013.01); *A61M 2230/20* (2013.01); *H05B 2203/021* (2013.01)

(56) References Cited

U.S. PATENT DOCUMENTS

| | | | | |
|---|---|---|---|---|
| 6,543,443 | B1* | 4/2003 | Klimowicz | A61M 15/0085 128/200.14 |
| 6,958,691 | B1* | 10/2005 | Anderson | A61B 5/0002 340/539.12 |
| 9,271,528 | B2* | 3/2016 | Liu | A24F 47/008 |
| 9,423,152 | B2* | 8/2016 | Ampolini | A24F 47/008 |
| 2003/0111088 | A1* | 6/2003 | Fox | A24F 47/002 131/273 |
| 2003/0168057 | A1* | 9/2003 | Snyder | A61M 15/0065 128/200.21 |
| 2005/0263618 | A1* | 12/2005 | Spallek | A61M 15/0065 239/433 |
| 2009/0084865 | A1* | 4/2009 | Maharajh | A61M 11/041 239/1 |
| 2010/0250280 | A1* | 9/2010 | Sutherland | A61M 15/0065 705/3 |
| 2011/0265806 | A1 | 11/2011 | Alarcon et al. | |
| 2012/0260927 | A1 | 10/2012 | Liu | |
| 2012/0291791 | A1* | 11/2012 | Pradeep | A24F 47/008 131/273 |
| 2012/0304990 | A1* | 12/2012 | Todd | A61M 11/042 128/203.14 |
| 2013/0192615 | A1 | 8/2013 | Tucker et al. | |
| 2014/0000638 | A1* | 1/2014 | Sebastian | A24F 47/008 131/328 |
| 2014/0041655 | A1* | 2/2014 | Barron | A61M 11/042 128/202.21 |
| 2014/0060527 | A1* | 3/2014 | Liu | A61M 15/06 128/202.21 |
| 2014/0060556 | A1* | 3/2014 | Liu | A24F 47/008 131/329 |
| 2014/0190503 | A1* | 7/2014 | Li | A61M 15/06 131/329 |
| 2014/0261488 | A1* | 9/2014 | Tucker | A24F 47/008 131/328 |
| 2015/0047661 | A1* | 2/2015 | Blackley | H05B 3/12 131/329 |
| 2015/0047662 | A1* | 2/2015 | Hopps | A24F 47/008 131/329 |
| 2015/0164145 | A1* | 6/2015 | Zhou | A24F 47/008 131/329 |
| 2016/0360788 | A1* | 12/2016 | Wang | A24F 47/008 |

* cited by examiner

DEVICE FOR ADJUSTING AN AMOUNT OF AN ACTIVE SUBSTANCE INHALED BY A USER AND COMMUNICATING PORTABLE TERMINAL

RELATED APPLICATIONS

This application is a § 371 application from PCT/FR2015/050839 filed Mar. 31, 2015, which claims priority from French Patent Application No. 14 00817 filed Apr. 4, 2014, each of which is incorporated herein by reference in its entirety.

TECHNICAL FIELD OF THE INVENTION

The present invention relates to a device for adjusting an amount of an active substance inhaled by a user, and a communicating portable terminal. It applies, in particular, to weaning a smoker from nicotine by means of an electronic cigarette.

STATE OF THE ART

Use of an electronic cigarette is recognized as being one of the means of stopping a person's addiction to nicotine. However, in the current systems, the electronic cigarettes are likely to replace conventional cigarettes because these systems provide no weaning.

In the current systems, weaning a person from nicotine by means of an electronic cigarette is solely based on that person's capacity for self-control. It is well known that, because of the mechanisms of nicotine addition, the person's willpower alone is frequently inadequate in the long term.

OBJECT AND SUMMARY OF THE INVENTION

The present invention aims to remedy all or part of these drawbacks.

To this end, according to a first aspect, the present invention envisages a device for adjusting an amount of an active substance inhaled by a user, which comprises:
 two tanks, a first tank containing a liquid having a lower density of active substance than a liquid in the second tank, each liquid being configured to evaporate when said liquid is heated beyond a predefined temperature limit;
 a means for inhaling, by the user, the liquid vapor evaporating from each tank;
 two heating resistors, each tank being associated with one heating resistor;
 a means for determining an amount of active substance to be vaporized;
 a means for controlling the heating of each resistor in order to actuate each resistor independently in accordance with the determined amount of active substance to be vaporized, the ratio of the heating of the resistor associated with the second tank to the heating of the resistor associated with the first tank being an increasing function of the determined amount of active substance to be vaporized.

Thanks to these provisions, the amount of an active substance inhaled by a user of the device is regulated by heating the first or the second liquid, each of these liquids having a different density of active substance. In this way, for an amount of inhaled vapor that is identical for each inhalation, the proportion of active substance in the inhaled vapor differs for each inhalation.

In some embodiments, the device that is the subject of the present invention comprises a means for accessing a user profile, the means for determining an amount of active substance to be vaporized determining the amount according to data for the user profile.

The advantage of these embodiments is that they make it possible to adjust the amount of active substance according to a standard user profile or to a specific item of data for a user having entered an item of morphological and/or medical information into a profile.

In some embodiments, the determination means determines an amount of active substance to be vaporized as a function of an item of timestamp data related to a starting up of the device.

These embodiments have the advantage of making it possible to adjust the amount of active substance according to a time of day or week.

In some embodiments, the determination means determines an increasing amount of active substance, relative to the last amount of active substance determined, when the item of timestamp data is the first item of timestamp data greater than a predefined time.

The advantage of these embodiments is that they make it possible, in the morning for example, to increase the amount of active substance inhaled.

In some embodiments, the determination means determines a generally-decreasing amount of active substance as a function of the item of timestamp data.

These embodiments have the advantage of making the user's weaning possible.

In some embodiments, the device that is the subject of the present invention comprises a means for detecting the user's frequency of inhaling on the inhalation means, the determination means determining the amount of active substance as a function of the inhalation frequency detected.

The advantage of these embodiments is that they make it possible to increase the amount of active substance inhaled, when the user exhibits a marked lack of active substance, eg during an evening function.

In some embodiments, the device that is the subject of the present invention comprises a means for capturing the user's blood-alcohol level, the determination means determining the amount of active substance to be vaporized as a function of the blood-alcohol level captured.

These embodiments have the advantage, when a detected blood-alcohol level is below a predefined limit value, of allowing the concentration of active substance by inhalation to be increased or decreased.

In some embodiments, the device comprises a means for capturing an item of data representative of a temperature in at least one tank, the control means controlling the heating of the resistor associated with each said tank as a function of the temperature captured.

The advantage of these embodiments is that they make it possible to detect a malfunction of a resistor, for example. In addition, these embodiments make it possible to take each resistor's characteristic cooling time into account.

According to a second aspect, the present invention envisages a communicating portable terminal, which comprises:
 a means for determining an item of information representative of an amount of active substance to be vaporized; and
 a means for transmitting, to a device that is the subject of the present invention, the item of information representative of an amount of active substance to be vaporized that is the subject of the present invention.

As the particular features, advantages and aims of this communicating portable terminal are similar to those of the device for adjusting an amount of an active substance to be inhaled that is the subject of the present invention, they are not repeated here.

BRIEF DESCRIPTION OF THE FIGURES

Other advantages, aims and particular features of the invention will become apparent from the non-limiting description that follows of at least one particular embodiment of the device and terminal that are the subjects of the present invention, with reference to drawings included in an appendix, wherein.

DETAILED DESCRIPTION OF THE EMBODIMENTS

The present description is given as a non-limiting example, each characteristic of an embodiment being able to be combined with any other characteristic of any other embodiment in an advantageous way. In addition, each parameter of an example of realization can be utilized independently from the other parameters of said example of realization.

It is noted that the terms "one, a; an" are used in the sense of "at least one".

It is now noted that the figures are not to scale.

It is now noted that the term "active substance" refers, in a non-limiting way, to any therapeutic active substance and to nicotine, for example.

Figure 1:
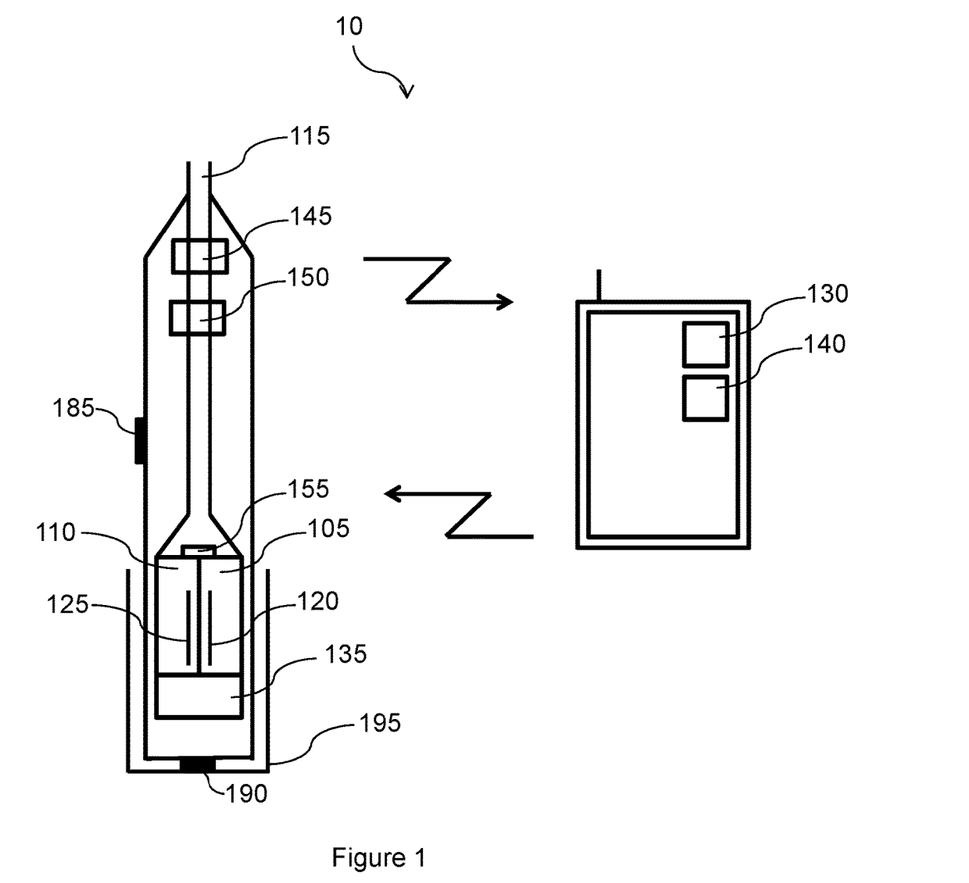
FIG. 1 represents, schematically and in cross-section, a first particular embodiment of the device that is the subject of the present invention.

FIG. 1, which is not to scale, shows a cross-section view of an embodiment of the device 10 that is the subject of the present invention. This device 10 comprises:

- two tanks 105 and 110, a first tank 105 comprising a liquid having a lower density of active substance than a liquid in the second tank 110, each liquid being configured to evaporate when said liquid is heated beyond a predefined temperature limit;
- a means 115 for inhaling, by the user, the liquid vapor evaporating from each tank, 105 and 110;
- two heating resistors, 120 and 125, each tank, 105 and 110, being associated with one heating resistor, 120 and 125;
- a means 130 for determining an amount of active substance to be vaporized;
- a means 135 for controlling the heating of each resistor, 120 and 125;
- a means 140 for accessing a user profile;
- a means 145 for detecting the user's frequency of inhaling on the inhalation means 115,
- a means 150 for capturing the user's blood-alcohol level; and
- a means 155 for capturing an item of data representative of a temperature in at least one tank, 105 and 110.

The two tanks, 105 and 110, are, for example, two tanks with identical dimensions configured to be transportable in a device with dimensions comparable to those of an electronic cigarette. These tanks, 105 and 110, for example have dimensions for containing 6 mL of liquid each. Each of these tanks, 105 and 110, comprises a cavity, not shown, allowing a heating resistor, 120 and 125, to be inserted. A heating resistor, 120 and 125, is associated with each tank, 105 or 110, such that when a heating resistor, 120 or 125, is heated, only the liquid contained in the associated tank, 105 or 110, is heated.

In some variants, the two tanks, 105 and 110, are positioned parallel to each other along a longitudinal axis of a tube generally in the shape of a cylinder of revolution. This tube comprises the inhalation means 115, downstream from a side of the air channel passing via an outlet of each tank, and an air inlet, not shown, upstream from the air channel.

In some variants, the device 10 comprises at least three tanks.

The inhalation means 115 is, for example, a duct configured to allow a user to inhale the vapors exiting from the tanks, 105 and 110.

The two resistors, 120 and 125, are, for example, electrical resistors heating by Joule effect when a current is applied to these resistors. The heating of such a resistor, 120 and 125, depends upon the amperage of the current passing through said resistor, 120 and 125. Therefore, the heating of the resistor, 120 and 125, can be regulated by a control means 135 configured to apply current of a determined amperage to this resistor, 120 et 125.

The determination means 130 is, for example, a computer program incorporated in a communicating portable terminal and/or in the device comprising the tanks, 105 and 110. This communicating portable terminal is, for example, a smartphone or a digital tablet. This determination means 130 comprises a means 140 for accessing a user profile. This user profile corresponds to a standard user profile determined as a function of the user's declared or learned consumption data. These consumption data comprise, for example:

- a consumption frequency as a function of a time of day or week;
- a typical time of a day of consumption; and
- distribution of the inhalation of an active substance from an electronic cigarette or from a cigarette.

Where the consumption data are learned, these data are obtained by accumulating memorized data relating to use of the control means. During a learning period, the control means is, for example, configured to control the vaporization of a constant amount of the active substance. Each inhalation is dated by a timestamping means, such as an electronic clock. Data representative of each inhalation are transmitted to a memory by means of a transmission means. This transmission means is, for example, an antenna configured to emit a wireless signal using Bluetooth technology. In some variants, the memory is in the same housing as the inhalation means. In other variants, the memory is incorporated into the communicating portable terminal. In other variants, the memory is remote.

Based upon memorized data, a means for determining a user profile determines a user profile. This means for determining a user profile is, for example, a computer program configured to compare a graph of active substance consumption over time, on the scale of a day and/or a week, to standard consumption graphs. When a standard consumption graph that is the closest to the learned consumption graph is determined, the means for determining a user profile determines that the user profile associated to this standard graph corresponds to the standard profile of the user whose mode of consumption has been learned.

The access means 140 is, for example, an antenna configured to communicate with a remote server holding data related to the user profile.

The determination means 130 is configured to determine an amount of an active substance to be vaporized as a function of a standard weaning graph associated to the standard user profile determined. This graph generally decreases over time on a scale of a week, for example. However, this graph can increase at certain times in a day or a week based upon the user's noticed habits of consumption.

An item of timestamp data is linked to a determination time by the determination means 130. This item of timestamp data is obtained, for example, by an electronic clock configured to measure an activation date and time of one of the means of the device 10.

The means 130 for determining an amount of active substance to be vaporized determines the amount as a function of the user profile data.

The determination means 130 determines an amount of active substance to be vaporized as a function of an item of timestamp data related to a starting up of the device 10.

The determination means 130 determines an increasing amount of active substance, relative to the last amount of active substance determined, when the item of timestamp data is the first item of timestamp data greater than a predefined time. For example, the first inhalation of the day has a greater amount of active substance than the last inhalation of the previous day.

In some variants, the determination means 130 determines an increasing amount of active substance when a length of time longer than a predefined limit time has elapsed since the last inhalation.

The determination means 130 determines a generally-decreasing amount of active substance as a function of the item of timestamp data.

The means 145 for detecting the user's frequency of inhaling on the inhalation means 115 is, for example, an electronic circuit comprising a counter of the number of the inhalations completed by the user on the inhalation means 115. The number of inhalations is determined, for example, by using a propeller configured to turn when the air passes through the duct of the inhalation means 115 in a predefined direction. This number of inhalations, measured over a rolling predefined limit time, divided by the rolling predefined limit time, gives an inhalation frequency.

When this inhalation frequency is greater than a predefined limit frequency, the determination means 130 determines an increasing amount of active substance to be vaporized, relative to the previous amount of active substance determined. Generally, the determination means 130 determines the amount of active substance as a function of the inhalation frequency detected.

The device 10 comprises a means 150 for capturing the user's blood-alcohol level. This capture means 150 is, for example, an alcohol sensor connected to the inhalation means 115.

The determination means 130 determines the amount of active substance to be vaporized as a function of the blood-alcohol level captured. If the blood-alcohol level captured is high and an item of data, variable or not, of the user profile indicates that the user is a driver, the determined amount of active substance is increased. Conversely, if the user profile indicates that the user is not a driver, the determined amount of active substance is reduced.

In some variants, the determination means 130 is incorporated into the same housing as the inhalation means 115. In other variants, the determination means 130 is in a remote memory, such as a server for example.

The determined amount of active substance to be vaporized is sent, by a means for emitting an item of information representative of the determined amount of active substance, towards to control means 135. This emission means is, for example, an antenna of the communicating portable terminal comprising the determination means 130 configured to emit a signal using Bluetooth technology.

The control means 135 is, for example, a microcontroller connected to a stand-alone power supply, not shown. The control means 135 transmits an electrical current to each resistor, 120 and 125, according to the determined amount of active substance to be vaporized.

In some variants, the stand-alone power supply is charged by a dynamo positioned on the air channel inside the duct and activated by the passage of air by means of a propeller for example.

The means 135 for controlling the heating of each resistor, 120 and 125, in order to actuate each resistor, 120 and 125, independently in accordance with the determined amount of active substance to be vaporized, the ratio of the heating of the resistor 125 associated with the second tank 110 to the heating of the resistor 120 associated with the first tank 105 being an increasing function of the determined amount of active substance to be vaporized.

This control means 135 transmits an electrical current according to the liquids present in each tank, 105 and 110. The nature of these liquids can be transmitted by the communicating portable terminal.

In some variants, the device 10 comprises a button having two states. In a first state, the control means 135 is inhibited and regulation of the amount of active substance does not occur. In a second state, the control means 135 operates as described above. This button can be replaced by an antenna for receiving a command contained in a wireless signal emitted, for example, by the communicating portable terminal.

In some variants, the device 10 comprises a rotating ring, whose degree of rotation determines an amount of active substance to be vaporized, or a heating ratio for the two resistors, 120 and 125.

In some variants, the device 10 comprises a rotating ring, whose degree of rotation determines an overall heating power for the two resistors, 120 and 125.

In some variants, the rotating rings are combined and a button (not shown) makes it possible to pass from determining the overall power to determining the amount of the substance. This button can be replaced by an antenna for receiving a command contained in a wireless signal emitted, for example, by the communicating portable terminal.

In some variants, the rotating ring or the button is replaced by a touch area 185, a finger movement by the user on this touch area making it possible to adjust the level of active substance to be evaporated. For example:
- if the user sweeps the touch area 185 towards an aspiration nozzle, the amount of nicotine to be evaporated is increased;
- if the user sweeps the touch area 185 towards an extremity opposite the aspiration nozzle, the amount of nicotine to be evaporated is reduced;

if the user sweeps the touch area 185 towards a first side of the device 10, the heating power ratio of a first resistor relative to the heating power of the second resistor is increased; and if the user sweeps the touch area 185 towards a second side of the device 10, the heating power ratio of the first resistor relative to the heating power of the second resistor is reduced.

The device 10 comprises a means 155 for capturing an item of data representative of a temperature in at least one tank, 105 and 110. This capture means 155 is, for example, an electronic thermometer.

The control means 135 controls the heating of the resistor, 120 and 125, associated with each said tank, 105 and 110, according to the temperature captured.

In some variants, the device 10 comprises a means for capturing the inhalation flow-rate of a user. This means for capturing the flow-rate is, for example, an electronic circuit connected to a propeller positioned in the duct. On the basis of a captured rotation of the propeller and of a predefined value representative of the surface area of the cross-section of the duct at the location of the propeller, the means for capturing the flow-rate calculates the inhalation flow-rate.

In some variants, the device 10 comprises a means for emitting the user's consumption information to a remote memory. This emission means is, for example, an antenna configured to emit a wireless signal using, for example, standard IEEE 802.11, known as "Wi-Fi". The consumption information memorized in this way makes it possible, for example, to establish statistics transmitted to a communicating portable terminal of the user.

In some variants, the device 10 comprises a removable cover 195 for protecting the tanks, 105 and 110, this cover 195 comprising a means 190 for charging the electrical systems of the device 10. This charging means 190 is, for example, an electrically conductive shank, for example of micro-USB type, put into contact with a power supply shank (not shown) of the device 10. In some variants, this charging means 190 utilizes induction charging. This cover 195 comprises, for example, an electrical power supply, such as, for example, a cell or a battery.

In some variants, the device 10 comprises a screen for displaying information representative of:
a charge level of the battery;
a filling level of one or of each tank;
a mode of consumption, manual or automatic, of the active substance; and/or
a heating ratio between the two resistors;
a value of the resistors detected in Ohms;
wear of the resistors as a percentage;
a real-time temperature of the resistors;
a total power or total voltage at the terminals of each resistor;
a value of the heating power ratio between the resistors; and/or
various messages in the form of text.

In some variants, the device 10 comprises a means for emitting a light signal. This means for emitting a light signal is, for example, a light-emitting diode configured to emit light when a detected inhalation frequency of the user is higher than a predefined limit value.

In some variants, the control means 135 is deactivated during a predefined limit time when a predefined limit quantity of active substance has been vaporized during a predefined limit time.

In some variants, at least one of the tanks, 105 and 110, comprises a medicine configured to be taken orally or by inhaler. This medicine is, for example, in the form of large molecules broken up by a means for emitting ultrasounds.

In some variants, the determination means 130 determines an amount of active substance to be inhaled as a function of an item of information about an event, declared by the user, related to an item of timestamp data. When the determination of an amount of active substance occurred during the memorized event, the determined amount of active substance is increased.

In some variants, the inhalation means 115 is connected to a geolocation means and an item of data representative of a location is associated in a memory with each item of data for an inhalation.

In some variants, at least one emission means emitting a signal using Bluetooth technology utilizes Bluetooth Low Energy technology.

Figure 2:
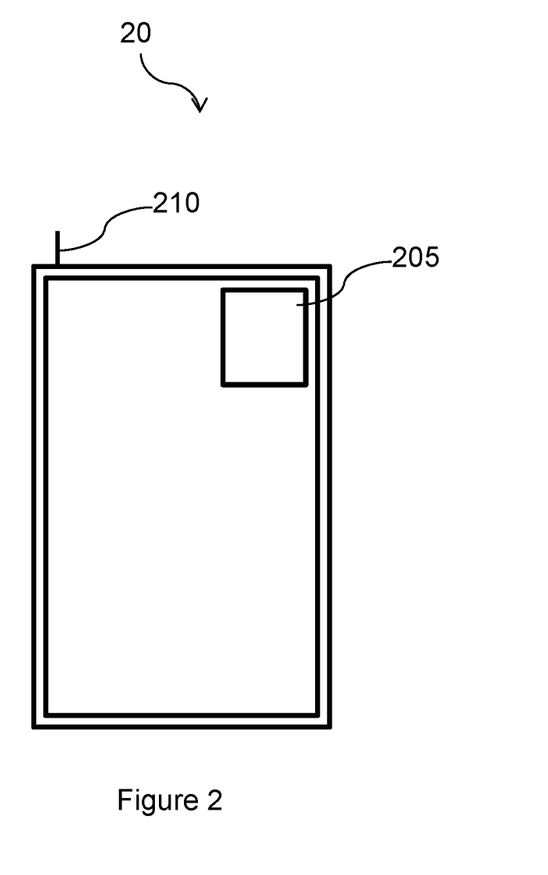
FIG. 2 represents, schematically and in cross-section, a particular embodiment of the terminal that is the subject of the present invention.

FIG. 2 shows a particular embodiment of the communicating portable terminal 20. This terminal 20 comprises:
a means 205 for determining an item of information representative of an amount of active substance to be vaporized; and
a means 210 for transmitting an item of information representative of an amount of active substance to be vaporized to a device 10, as described in FIG. 1.

The determination means 205 is similar to the determination means 130 described in FIG. 1.

The transmission means 210 is, for example, an antenna configured to emit a wireless signal using Bluetooth technology.

Figure 3:
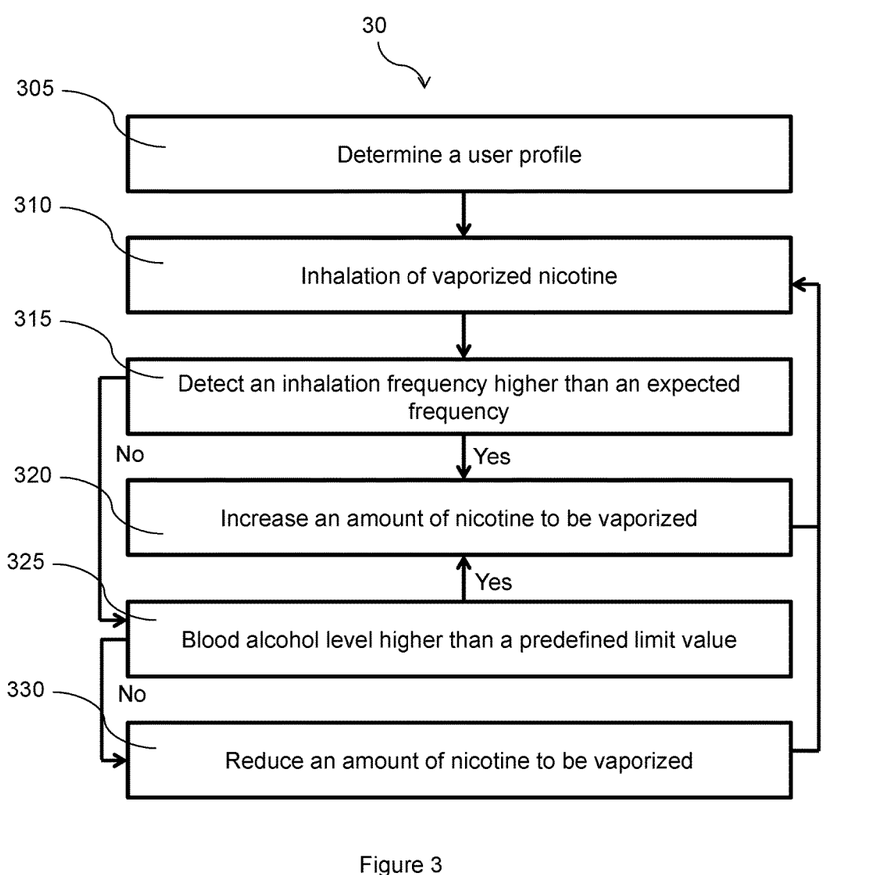
FIG. 3 represents, schematically and in cross-section, a logical diagram of particular steps of the method that is the subject of the present invention.

FIG. 3 shows a logical diagram of particular steps of the method 30 that is the subject of the present invention. This method 30 comprises a step 305 of determining a user profile and, iteratively:
a step 310 of inhaling a vaporized amount of active substance;
a step 315 of detecting an inhalation frequency higher than an expected frequency;
a step 320 of increasing an amount of active substance to be vaporized;
a step 325 of detecting a user's blood-alcohol level;
a step 330 of reducing an amount of active substance to be vaporized.

When a user equipped with the device 10 as described in FIG. 1 starts weaning off the active substance, this user is associated to a user profile. This user profile is either declared or learned.

In the variants where this user profile is declared, the user fills in, by means of a user interface such as, for example, an application of a communicating portable terminal, a number of predefined information fields. These information fields comprise, for example, information about a mode of consumption of the active substance, for example in terms of:
frequency;
consumption time; and
breakdown between electronic cigarette and cigarette.

Other information fields can comprise information relating to the user's morphological or medical data.

In the variants where this profile is learned, the device 10 memorizes the behavior of a user, as a function of timestamp data, without adjusting an amount of active substance vaporized during an inhalation of vapors by the user. The data memorized in this way make it possible, for example, to determine the times of day when the user most frequently inhales the active substance, and a normal schedule of consumption as a function of the day of the week. For example, a user may consume more active substance on Friday evenings than on Tuesday afternoons. In these variants, the learning performed can continue once the determination means starts to determine an amount of active substance to be vaporized.

This declared or learned user profile is associated, in some variants, to a predefined standard user profile. This standard user profile represents, in a general way, a certain mode of consumption of the active substance by a user. As described below, the weaning achieved depends upon this standard user profile associated to the user profile.

This user profile is stored, for example, in a memory of the communicating portable terminal. This communicating portable terminal is, for example, a smartphone or a digital tablet. In some variants, this user profile is stored, for example, in a memory associated to the determination means of the device 10. In other variants, this user profile is stored, for example, in a remote memory associated to the device 10, from which the determination means can obtain, via a wireless signal transmission, data for the stored profile.

When the user profile has been determined, the determination means of the device 10 determines an amount of active substance to be vaporized comparable to an amount of active substance normally consumed by the user, as a function of the standard user profile associated to the user.

Then, each new determination of an amount of active substance to be vaporized is generally lower than the amounts determined previously, so as to follow a standard weaning graph associated to the standard profile. This graph, although generally decreasing, can comprise temporary peaks of active substance on certain days of the week, for example. The determination means of the device 10 determines the amount of active substance to be vaporized as a function of a memory of amounts determined previously and a captured timestamp.

When a user's frequency of inhaling on the inhalation means of the device 10 is higher than a predefined limit frequency, the determination means is configured to determine an amount of active substance that is greater than the amount of active substance determined by the use of the standard graph.

When a captured blood alcohol level of a user of the device 10 is higher than a predefined limit value, the determined amount of active substance to be vaporized is greater than the amount of active substance determined by the use of the standard graph. Unlike alcohol, the active substance acts as a concentration means for the user. This concentration, when the user is, for example, driving a vehicle, makes it possible to avoid the risks of traffic accidents.

In some variants, the captured blood alcohol level is only considered if the user has declared, in the user profile, being a driver. In some variants, the device 10 comprises a means of switching between a declaration by the driver of having the status of driver or having the status of non-driver. This switching means is, for example, a button of a graphical interface of the communicating portable terminal of the device 10. Depending on the status selected, the determination means of the device 10 determines the amount of active substance as described above or not.

When an amount of active substance to be vaporized has been determined, an item of information representative of this determined amount of active substance is transmitted to a control means of the device 10. This control means is configured to actuate the heating of a first and/or a second resistor, each associated to a tank containing a liquid. A first tank contains a liquid having a lower density of active substance than a liquid in the second tank. This control means is, for example, an electronic circuit connected to a means for receiving the item of information representative of an amount of active substance to be vaporized. This reception means is, for example, an antenna configured to receive a wireless signal emitted by an emission means associated to the determination means.

In some variants, one of the tanks contains a liquid, a vaporized element of which reacts with the nicotine contained in a cigarette to produce a disagreeable taste and/or odor.

In some variants, each tank contains a liquid with a different taste, the device 10 aiming to allow the taste of the vapor to be adjusted. This adjustment can be obtained by using two tanks simultaneously, or one after the other.

According to the item of information about the determined amount of active substance received, the control means of the device 10 controls the activation of the first and/or second resistor such that the volume of vapor is identical, between two inhalations, and the amount of active substance in this volume is different. When a larger quantity of vapor of the first liquid, having a lower density of active substance, is vaporized, the total vapor formed by the sum of the vapors from each tank has an amount of active substance that is reduced in relation to a vapor solely comprising vapor from the second tank.

Figure 4:
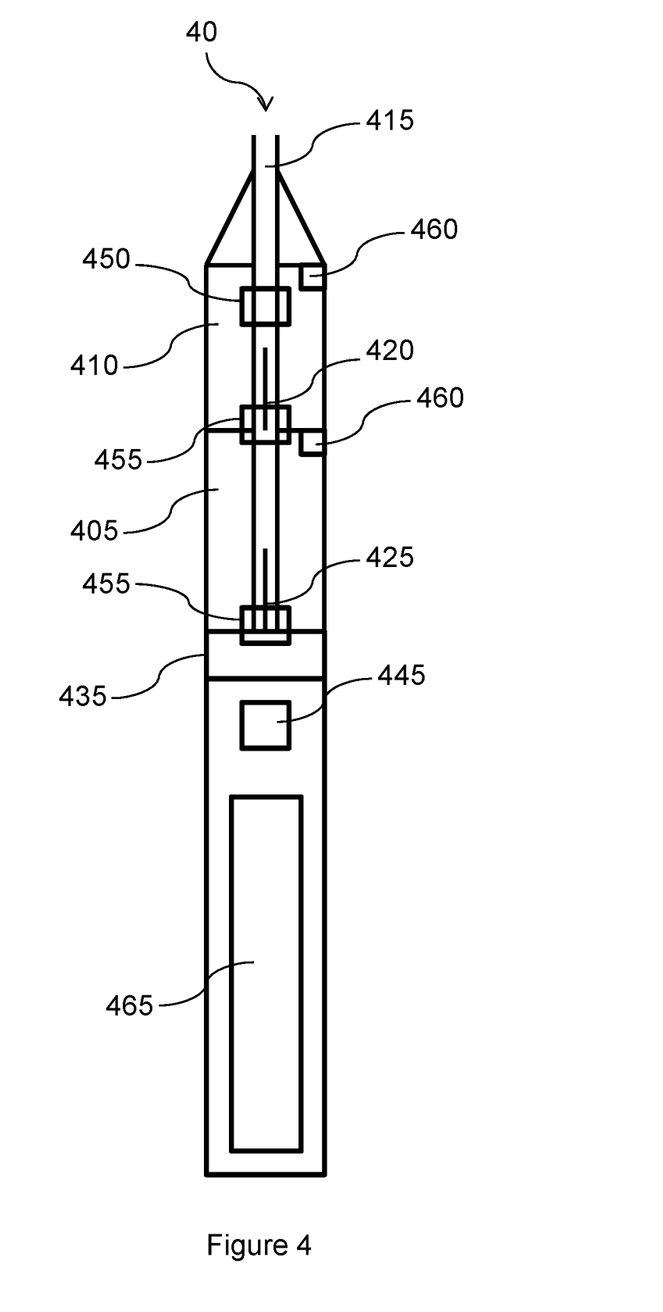
FIG. 4 represents, schematically and in cross-section, a second particular embodiment of the device that is the subject of the present invention.

FIG. 4 shows a particular embodiment of the device 40 that is the subject of the present invention. The references 405, 410, 415, 420, 425, 435, 445, 450 and 455 correspond, for example, to references 405, 110, 115, 120, 125, 135, 145, 150 and 155 described with regard to FIG. 1.

In this embodiment, the tanks, 405 and 410, are arranged in steps, a resistor, 420 and 425, being positioned in each tank, 405 and 410. In this embodiment, the device 40 comprises a means 455 for capturing the temperature for each tank, 405 and 410.

In this embodiment, the device 40 comprises two removable elements. One element, called the "lower" element, comprises a battery 165 and the detection means 145.

In this embodiment, each tank, 105 and 110, comprises an air-tight valve for injecting liquid allowing liquid to pass in a single direction to the inside of said tank, 105 or 110. This valve enables, in particular, a nozzle of a vial of liquid for an electronic cigarette to be inserted.

Figure 5:
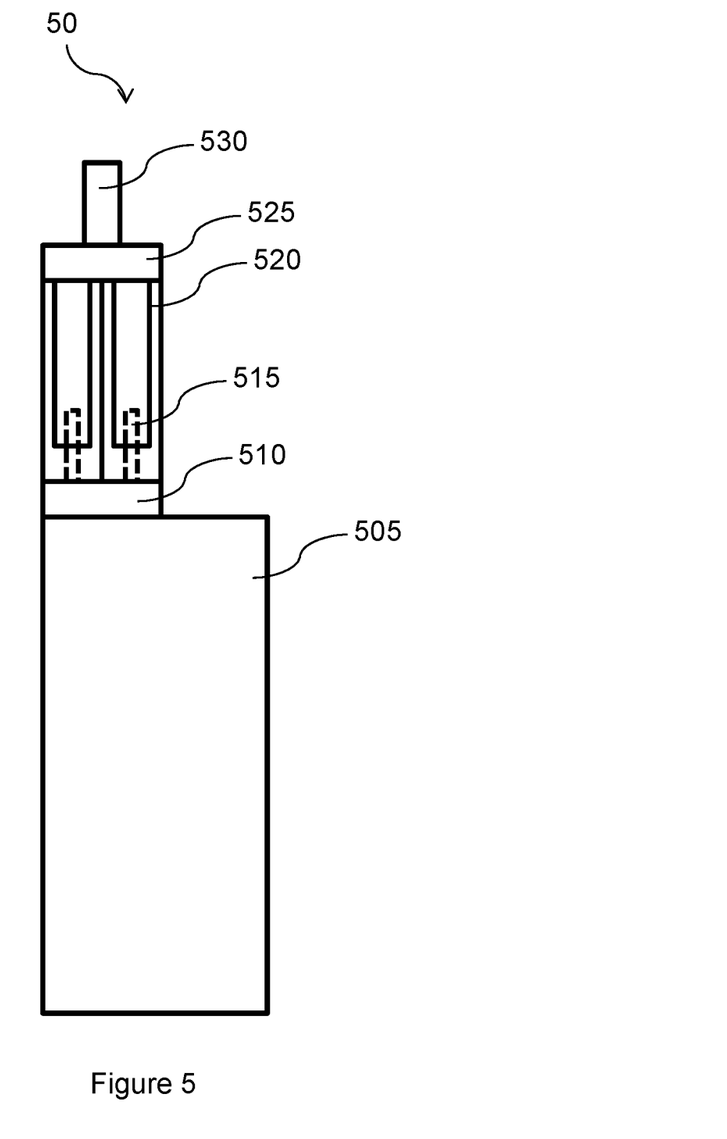
FIG. 5 represents, schematically and in cross-section, a third particular embodiment of the device that is the subject of the present invention.

FIG. 5 shows a third particular embodiment of the device 50 that is the subject of the present invention. This device 50 comprises:
- a housing 505 comprising a battery (not shown) powering the electrical systems of the device 50;
- a connection ring 510 screwed onto the housing 505;
- a tank 520 comprising several compartments;
- for each compartment, a vaporizer 515 screwed onto the ring 510 and embedded in the tank 520 opposite the corresponding compartment;
- a vapor mixing chamber 525 fixed to the tank 520, this chamber comprising, in some variants, valves (not shown) for injecting liquid into the compartments; and
- an aspiration nozzle 530 for vapors.

In some embodiments (not shown), the present invention envisages a device similar to device 10 or device 40 adapted for the consumption of morphine as the active substance.

In some embodiments (not shown), the present invention envisages a device similar to device 10 or device 40, adapted for the consumption of THC as active substance.

In some embodiments (not shown), the present invention envisages a device similar to device 10 or device 40, adapted for the consumption of an essential oil as active substance.

The invention claimed is:

1. A device to adjust an amount of an active substance inhaled by a user, comprising:
    a first tank comprising a first liquid having an active substance at a first density and being configured to evaporate when said liquid is heated beyond a predefined first temperature limit;
    a second tank comprising a second liquid having said active substance at a second density and being configured to evaporate when said second liquid is heated beyond a predefined second temperature limit, said first density is lower than said second density;
    an inhaler to inhale, by the user, a liquid vapor evaporating from said first and second tank;
    a first heating resistor associated with said first tank and being configured to heat said first liquid within said first tank beyond said first temperature limit, and a second heating resistor associated with said second tank and being configured to heat said second liquid within said second tank beyond said second temperature limit;
    a processor configured to determine a required amount of active substance to be vaporized during an inhalation, and to increase or decrease said required amount with respect to previous inhalations;
    a controller configured to control an amount of vaporized active substance by actuating said each first and second heating resistors independently in accordance with said required amount;
    wherein said controller is configured to set the heating of said second resistor and the heating of said first resistor such that the ratio between the heating of said second resistor and the heating of said first resistor is increased when said processor increases said required amount.

2. The device according to claim 1, further comprising a communication unit to access a user profile, the processor determines the required amount according to data from the user profile.

3. The device according to claim 1, wherein the processor is configured to increase or decrease said required amount with respect to previous inhalations in accordance with timestamp data related to said previous inhalations.

4. The device according to claim 3, wherein the processor determines an increasing amount of active substance, relative to a last amount of active substance determined, when the timestamp data is a first item of timestamp data greater than a predefined time.

5. The device according to claim 3, wherein the processor determines a decreasing amount of active substance as a function of the timestamp data.

6. The device according to claim 5, further comprising a detector to detect an inhalation frequency of inhaling on the inhaler by the user, and wherein the processor is configured to determine the amount of active substance as a function of the inhalation frequency.

7. The device according to claim 1, further comprising a sensor to capture a blood-alcohol level of the user; and wherein the processor is configured to determine the amount of active substance to be vaporized as a function of the blood-alcohol level of the user.

8. The device according to claim 1, further comprising a thermometer to capture an item of data representative of a temperature in at least one tank, and wherein the controller is configured to control the heating of the resistor associated with said each tank as a function of the captured temperature.

9. A communicating portable terminal, comprising:
    a terminal processor configured to determine an item of information representative of an amount of active substance to be vaporized; and
    a transmitter to transmit to a device according to claim 1, the item of information representative of an amount of active substance to be vaporized determined by the terminal processor.

* * * * *